United States Patent [19]
Tam

[11] Patent Number: 6,130,930
[45] Date of Patent: Oct. 10, 2000

[54] EXACT REGION OF INTEREST CONE BEAM IMAGING WITHOUT CIRCLE SCANS

[75] Inventor: Kwok Tam, Edison, N.J.

[73] Assignee: Siemens Corporate Research, Inc., Princeton, N.J.

[21] Appl. No.: 09/274,189

[22] Filed: Mar. 22, 1999

[51] Int. Cl.$^7$ ........................................ A61B 6/03
[52] U.S. Cl. ............................. 378/4; 378/15; 378/94
[58] Field of Search ............................ 378/4, 15, 901

[56] References Cited

U.S. PATENT DOCUMENTS

| | | | |
|---|---|---|---|
| 5,390,111 | 2/1995 | Tam | 378/16 |
| 5,390,226 | 2/1995 | Tam | 378/8 |
| 5,504,792 | 4/1996 | Tam | 378/15 |
| 5,748,697 | 5/1998 | Tam | 378/19 |

OTHER PUBLICATIONS

Region–of–Interest Cone Beam CT With A Spiral Scan, Tam et al., SPIE Conf. on Physics of Medical Imaging, San Digeo, CA, Feb. 1998, pp. 274–283.
U.S. Pat. Application Ser. No. 09/052,281 entitled "Exact Region of Interest Cone Beam Imaging Using 3D Backprojection", Kwok Tam, filed Mar. 31, 1998.

*Primary Examiner*—David V. Bruce
*Attorney, Agent, or Firm*—Lawrence C. Edelman

[57] ABSTRACT

A scanning and data acquisition method and apparatus for three dimensional (3D) computerized tomography (CT) imaging of an ROI in an object, wherein data is calculated on a plurality of line segments L formed in cone beam projection data acquired on a detector at a plurality of source positions. The endpoints of the line segments L formed in the data acquired at each of the source positions is determined by a data combination mask having its bounds formed by cone beam projection onto the plane of the detector of portions of the source scan path that are above and below the source position that acquired the cone beam data in which the data for the line segments L are being calculated. When processing cone beam data near the top or bottom edges of the ROI, a first group of the line segments L has both of its endpoints determined by the boundaries of the data combination mask, and a second group of the line segments L has one of its endpoints determined by a boundary of the data combination mask, and another of its endpoints determined by the x-axis of the mask, so as to avoid data corruption from x-rays that passed outside the ROI. The line integral data calculated for both groups of the line segments L formed in the mask are then processed using an image reconstruction technique for providing a contribution to a 3D image reconstruction of the ROI in the object.

19 Claims, 9 Drawing Sheets

EXACT REGION OF INTEREST CONE BEAM IMAGING WITHOUT CIRCLE SCANS

BACKGROUND OF THE INVENTION

1. Field of the Invention

The invention relates generally to exact image reconstruction in a cone beam computed tomography imaging system having a radiation source scan path that encircles a region of interest (ROI) in an object, and more specifically to such a cone beam imaging system wherein the source scan path does not require circle scans at the ends of the ROI.

2. Description of the Prior Art

Recently a system employing cone beam geometry has been developed for three-dimensional (3D) computed tomography (CT) imaging that includes a cone beam x-ray source and a 2D area detector. An object to be imaged is scanned, preferably over a 360° angular range and along its entire length, by any one of various methods wherein the position of the area detector is fixed relative to the source, and relative rotational and translational movement between the source and object provides the scanning (irradiation of the object by radiation energy). The cone beam approach for 3D CT has the potential to achieve 3D imaging in both medical and industrial applications with improved speed, as well as improved dose utilization when compared with conventional 3D CT apparatus (i.e., a stack of slices approach obtained using parallel or fan beam x-rays).

As a result of the relative movement of the cone beam source to a plurality of source positions (i.e., "views") along the scan path, the detector acquires a corresponding plurality of sequential sets of cone beam projected data (referred to hereinafter as cone beam data), each set of cone beam data being representative of x-ray attenuation caused by the object at a respective one of the source positions.

There are two basic approaches for processing the acquired cone beam data for reconstructing a 3D image of the object. The traditional approach is "Radon space driven", wherein the acquired sets of cone beam data are processed so as to develop a multitude of individual samples of Radon data for filling a Radon space "region of support" for the object. Once a sufficient amount of Radon space data has been developed, contributions to the final image reconstruction can begin. A newer approach is "detector data driven", where the individual sets of the acquired cone beam data (i.e., the detector data) are processed for directly developing successive contributions to the final image reconstruction (i.e., without the requirement of being transformed through Radon space). No matter which approach is used, the "processing" of the acquired cone beam data begins with a step that calculates line integral derivatives for a plurality of line segments L formed in the cone beam data. Detector driven image reconstruction processing is generally more desirable than Radon space driven processing because image reconstruction is more directly developed and therefore less system memory is required. In either case, the acquisition of the cone beam data is complete only if it can be processed so as to reconstruct the object with the desired resolution, and without artifacts. In the Radon space driven approach, this means developing a sufficient density of Radon data in a so-called "region of support" (a region which topologically corresponds to the field of view occupied by the region of interest in the object in real space). Typically, sufficient Radon data is acquired by exposing the entire object within the field of view to the radiation source.

Sufficient filling of the Radon space by cone beam CT apparatus having various scanning trajectories (paths) and using an area detector having a height which is less than the height of a region of interest (ROI) in the object being imaged, are known for performing an exact image reconstruction. For example, U.S. Pat. No. 5,463,666 entitled HELICAL AND CIRCLE SCAN REGION OF INTEREST COMPUTERIZED TOMOGRAPHY issued Oct. 31, 1995, describes a Radon space driven technique for imaging an ROI in an object without blurring or artifact introduction by providing a scan path consisting of a central spiral portion having a circle portion at its upper and lower ends, respectively, which are level with upper and lower boundaries of the ROI in the object. The witch from a spiral scan path to a circular scan path is necessary in order to obtain complete cone beam data at the upper and lower boundaries of the region of interest without overlap, thereby avoiding image blurring or artifacts which result from imaging portions of the object that are not within the ROI, as described in greater detail in the forenoted U.S. Pat. No. 5,463,666.

Although the above and other techniques have been useful, they require scan paths having both spiral and circular path portions, and necessarily results in abrupt shifts in movement of the scanning equipment portion of the imaging apparatus. Such abrupt shifts in scan movement are undesirable in that they either subject the patient to undesired jostling, or subject the scanning equipment to extra mechanical stress. It would be desirable to provide only a smoothly changing scan path. Furthermore, due to the use of circle and spiral scan path portions, a rather complex signal processing technique is required in order to avoid the combination of overlapping data on a given integration plane. It would be desirable to reduce the complexity of such signal processing required for image reconstruction.

U.S. patent application Ser. No. 09/052,415 entitled PRACTICAL CONE BEAM IMAGE RECONSTRUCTION USING LOCAL REGIONS-OF-INTEREST, filed Mar. 31, 1998, describes a Radon space driven technique for imaging an ROI in an object wherein the imaging equipment does not have the requirement to provide circle scans at the top and bottom of the ROI. As described therein, this is accomplished by processing the acquired cone beam data to develop specific sub-sets of Radon space data. Each of the sub-sets of Radon space data is targeted for reconstructing a corresponding "local 2D ROI" in a 2D parallel projection of the object on one of a plurality of vertically oriented coaxial φ-planes that partitions the Radon space. After a targeted sub-set of Radon data is developed, it is subjected to a first inversion processing step for developing the corresponding local 2D ROI projection image. Thereafter, multiple ones of the local 2D ROI projection images are grouped together and subjected to a second inversion processing step, thereby developing an image reconstruction of a portion of the 3D region of interest in the object. This process is repeated until the entire ROI in the object is reconstructed. By targeting specific subsets of Radon data for processing, the local 2D ROI projection images do not suffer from data corruption from overlaying objects, thereby allowing the use of a simplified scan path having only a spiral portion for traversing the ROI. Although this image reconstruction technique simplifies the scan path, reduces the memory requirements and improves the speed of the imaging system, the image reconstruction processing is still rather complex and the system memory requirements are still great.

U.S. patent application Ser. No. 09/052,281 entitled EXACT REGION OF INTEREST CONE BEAM IMAGING USING 3D BACKPROJECTION, filed Mar. 31, 1998, incorporated by reference herein, describes a detector driven technique called Filtered Backprojection (FBP) for reconstructing a 3D image of an ROI in an object. In this 3D backprojection technique, a first image reconstruction processing step calculates line integral derivatives for a plurality of line segments L formed in the cone beam data acquired at each source position. The extent of the line segments L in the data acquired at each of the source positions is determined by a data combination mask having its upper and lower bounds formed by cone beam projection onto the plane of the detector of portions of the source scan path that are above and below the source position that acquired the cone beam data in which the line integral derivatives for the line segments L are being calculated. In the next step, the calculated line integral derivatives for the line segments L are backprojected onto a 2D space corresponding to the plane of the detector. In the last step, the results of the 2D backprojecting step are 3D backprojected into a 3D space, each 3D backprojection provides a partial reconstruction of a 3D image of the object. Although the imaging equipment is still required to provide a circle scan path at the top and bottom of the ROI in the object to avoid image blurring or artifact introduction, the described masking/3D backprojection detector driven technique greatly reduces the complexity and memory requirements for image reconstruction signal processing as compared with Radon space driven image reconstruction techniques.

It would be desirable to provide exact image reconstruction processing which does not have the requirement of circle scan paths at the top and bottom edges of the ROI, and it would be particularly desirable that such processing be detector data driven. Such image reconstruction processing would be exact, less complex than the current Radon space driven processing, and subject neither the imaging equipment nor the patient to the abrupt shifts and stress of a segmented scan path.

SUMMARY OF THE INVENTION

In accordance with the principles of the present invention, the 3D backprojection technique of the forenoted U.S. patent application Ser. No. 09/052,281 is modified so as to allow an exact image reconstruction without the requirement of top and bottom circle scans, and so it is not limited to use of the 3D backprojection technique. In the inventive image reconstruction technique, the line segments L formed in the masked cone beam data are divided into separate groups for processing according to how their length is to be limited. More specifically, when processing line segments L formed in the cone beam data acquired near the top or bottom edges of the local ROI, a first group of the line segments L has both of its end points determined by the boundaries of the data combination mask, while a second group of the line segments L has one of its end points determined by one of the upper or lower boundaries of the mask, and its other end point determined by the horizontal (x-axis) of the mask. Thereafter, data calculated for both groups of the line segments L formed in the mask are processed so as to develop contributions to a 3D image reconstruction of the ROI in the object.

DETAILED DESCRIPTION OF THE INVENTION

Figure 1:
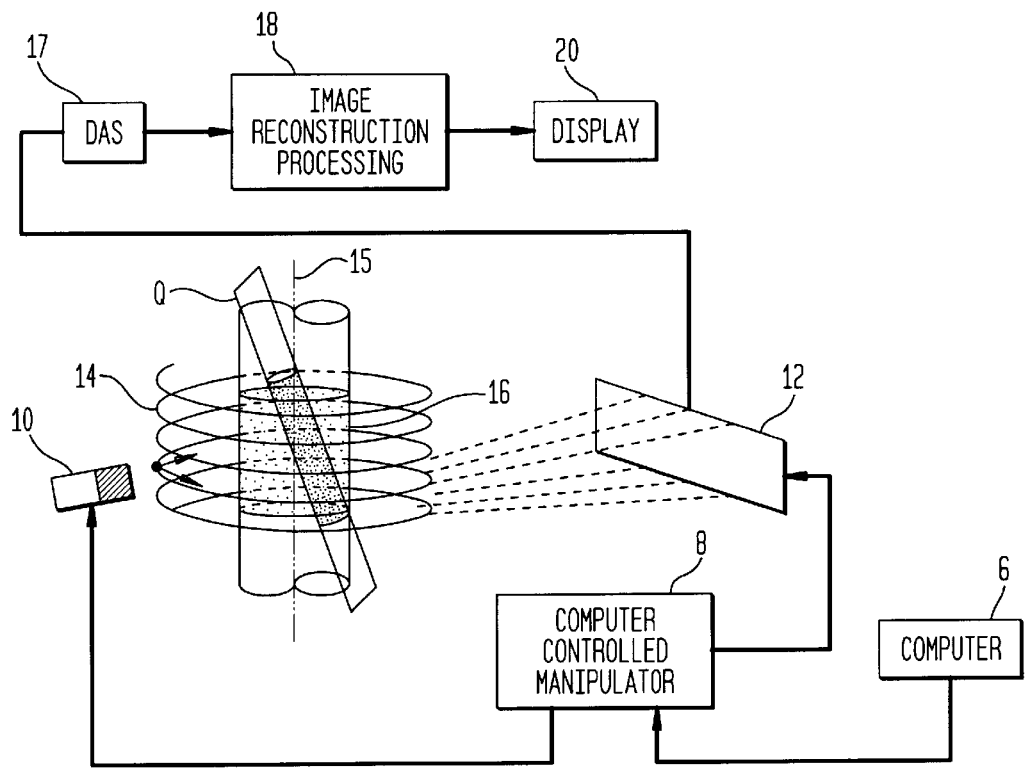
FIG. 1 illustrates a 3D CT imaging apparatus having a cone beam x-ray source, useful for acquiring and processing cone beam data in accordance with the principles of the present invention.

FIG. 1 illustrates a cone beam 3D CT imaging apparatus useful for acquiring and processing acquired cone beam data in accordance with the principles of the present invention. The illustrated imaging apparatus is constructed and operates substantially in accordance with same principles described in U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993 and U.S. Pat. No. 5,453,666 entitled HELICAL AND CIRCLE SCAN REGION OF INTEREST COMPUTERIZED TOMOGRAPHY issued Oct. 31, 1995, incorporated herein by reference, except that:

1) the source scan path does not require circle scans at the top and bottom portions of a region of interest (ROI), and
2) image reconstruction processing in accordance with the present invention uses a data combination mask technique, as will be more specifically described.

As shown in FIG. 1, a computer controlled manipulator 6, in response to control signals from an appropriately programmed computer 8, cause a source 10 of a cone or pyramid shaped beam of energy (such as x-rays) and a two-dimensional pixelated detector array 12 to cooperate (scan) at a plurality of discreet, sequentially occurring adjacent source positions, along a pre-defined source scanning path. In the illustrated embodiment the scanning path is shown as a spiral scan path 14 centered on a predetermined axis 15 of an object 16, and which proceeds in a counter-clockwise direction. Other types of scan paths that encircle and traverse object 16 can also be used, however, as will become apparent later, a scan path 14 exhibiting a high degree of symmetry in its parallel projection is preferred.

The only height requirement on the detector is that it's height should be more than the distance between adjacent turns of a cone beam projection of the spiral scan path 14 onto the detector 12. In accordance with the principles of the invention, and for reasons which will become evident later, if only an ROI (shaded area) of object 16 is to be imaged, the known technique of providing a top and bottom circle scan at the top and bottom ends, respectively, of the ROI, is not necessary. Thus, a simple continuous spiral scan path 14 that traverses the length of the ROI is all that is needed.

As a result of the source/detector cooperation under control of computer 6 and manipulator 8, at each of the source positions, beams of x-ray energy pass through the field of view of the imaging apparatus, are selectively attenuated by varying energy absorbing densities inside object 16, and a set of cone beam data corresponding to the sensed x-ray energy falling on the elements (pixels) of detector 12 are developed. The sets of cone beam data are then supplied to a data acquisition system (DAS) 17 which, like the previously described portions of FIG. 1, may operate in a fashion well known to those of ordinary skill in this technology for digitizing and storing of the acquired cone beam data.

As described in the present inventor's above-noted U.S. Pat. No. 5,257,183, image reconstruction processing 18 begins by calculating Radon derivative data from the acquired cone beam data, for those portions of integration planes Q that intersect the scan path and the ROI (one such Q-plane shown in FIG. 1). As described in detail in the '183 patent, Radon space driven conversion of the derivative data is used to develop an image reconstruction of object 16 on a display 20. The present inventor's U.S. Pat. No. 5,463,666 describes the use of data combination masks to improve the efficiency of the calculation of the Radon derivative data in such a Radon space driven technique. Alternatively, as will become apparent later, image reconstruction processing 18 of the present invention can also be detector data driven, such as the 3D backprojection technique described in the present inventor's forenoted U.S. patent application Ser. No. 09/052,281. In either case, however, in accordance with the principles of the present invention, image reconstruction processing 18 is modified, as described in greater detail below, so as to use data combination masks for more easily calculating the Radon derivative data from the acquired cone beam data.

In order to more fully understand the principles of the present invention, some review of the previously noted U.S. patent application Ser. No. 09/052,415 will be provided. As was noted above, this Radon space driven technique for ROI imaging does not have the requirement that imaging equipment provide circle scans at the top and bottom ends of the ROI. This is accomplished by processing the acquired cone beam data so as to develop specific sub-sets of Radon space data. Each of the sub-sets of Radon space data is targeted for reconstructing a corresponding "local 2D ROI" which is a 2D parallel projection of the object on individual ones of the plurality of vertically oriented coaxial φ-planes that partition the Radon space. Due to the nature of a parallel projection, the upper and lower bounds of the local 2D ROI projection images do not suffer data corruption from x-rays passing through areas outside the bounds of the local ROI. When a sufficient number of these local 2D ROI projection images are developed over 180 degrees (the sufficiency being determined by the desired resolution of the final image reconstruction), they are processed for directly developing contributions to the final image reconstruction, thereby obviating the requirement to provide circle scans at the top and bottom ends of the ROI.

Figure 2:
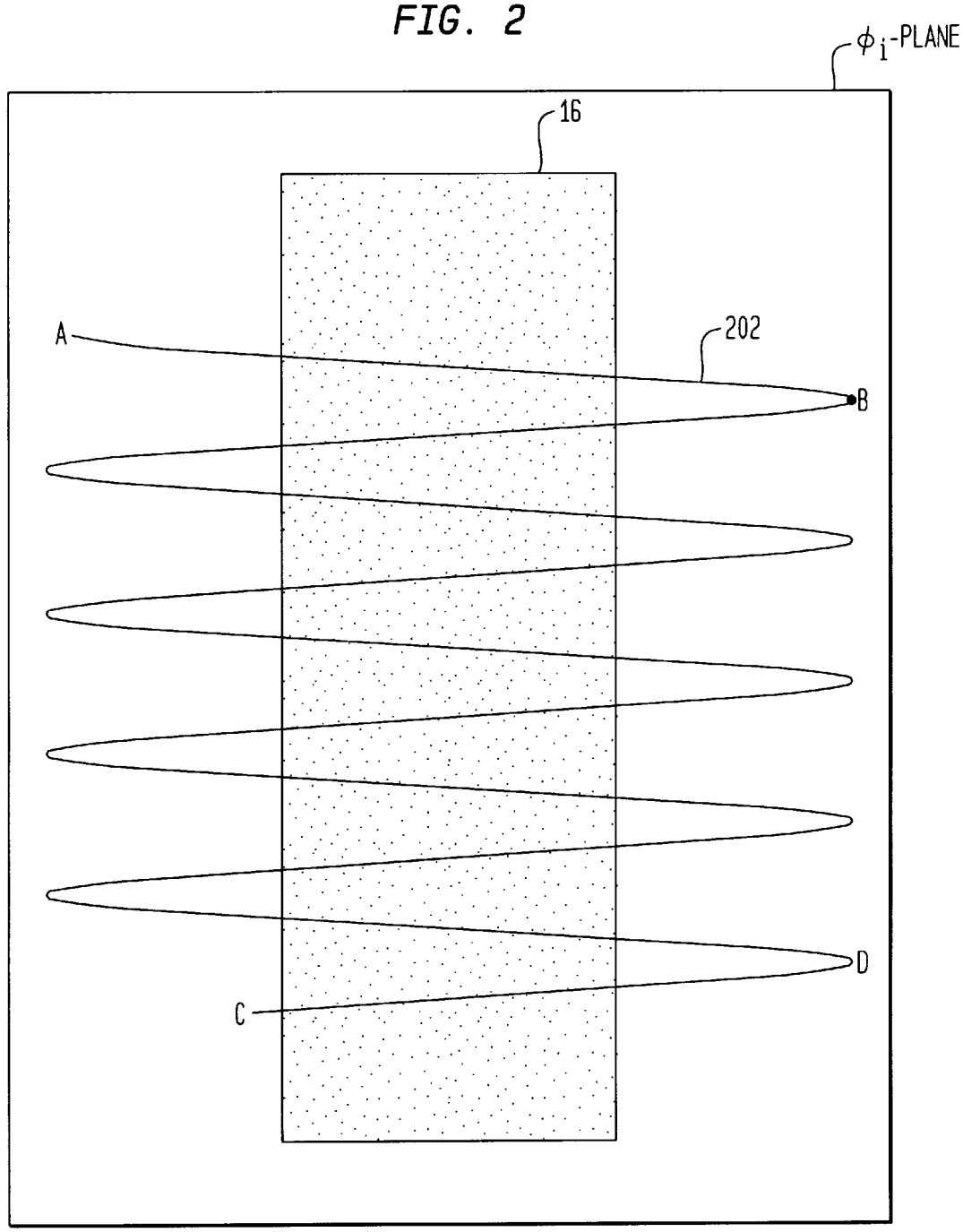
FIG. 2 illustrates a parallel projection of a source spiral scan path on a φ-plane, useful for understanding the local ROI technique of image reconstruction.

As noted above, the significance of this local ROI technique is that no circle scans are required at the top and bottom edges of the ROI in order to make an exact image reconstruction. Elimination of data corruption by overlaying materials at these edges of the ROI results from the fact that the relevant source positions reside on the uppermost and the lowermost stages of the parallel projection of the spiral path on each φ-plane. This concept and its significance is illustrated in FIG. 2, wherein a parallel projection of the spiral path 14 on a φ-plane is shown to manifest itself in the form of a sinusoidal curve 202 whose phase depends on the orientation of the φ-plane. For a given φ-plane where $\phi=\phi_i$, the uppermost and the lowermost turns of the projected spiral path 202, labelled AB and CD, respectively, in FIG. 2, define the upper and lower bounds of a "local" 2D ROI on that φ-plane. To ensure that the local ROI is completely separated from overlaying objects by the upper and lower bounds, the requirement for the angular range, or arc, of the uppermost and lowermost turns of spiral path 14 is that they each span at least $(\pi+\alpha)/2$ degrees, where $\alpha$ is the fan angle of the source. This range corresponds to a scan path projection, such as 202 of FIG. 2, having upper and lower ends (A and B) that begin and end, respectively, outside of the local ROI.

Thus, upon careful reflection, one can visualize that this prior art Radon space driven technique avoids blurring from objects outside the local ROI by appropriately restricting the cone beam data that is processed for computing the line integral derivatives, to that data which results by restricting the angular range of the x-ray paths to those that come from source positions which orthogonally project onto the uppermost and the lowermost stages of the projected spiral path. Note, this angular range restriction procedure (i.e., using the upper and lower boundaries of a local ROI) in this Radon space driven technique, is for a different reason (artifact rejection) and has a different effect than the data-combination mask procedure (i.e., using the upper and lower boundaries of a mask), which procedure is used to match portions of the cone beam data acquired from different source positions in order to make appropriate contributions to the derivative data of a common integration plane.

A difficulty in applying the benefits of the masking in the Radon space driven technique to the masking in the data-combination detector driven technique stems from the fact that there are some source positions, i.e. those near the top and bottom edges of the ROI, where a given source position orthogonally projects only onto the uppermost and the lowermost stages of the projected spiral path for only some of the φ-planes, and on other ones of the φ-planes, the given source position orthogonally projects onto the projected spiral path which is below the uppermost and above the lowermost stages. Thus the cone beam image data acquired at some source positions is required to be processed using two different procedures to take into account the Radon data on different φ-planes. In accordance with the principles of the present invention, a single processing procedure is provided which takes into account this requirement. This situation will now be described in greater detail in conjunction with FIGS. 3A and 3B.

Figure 4:
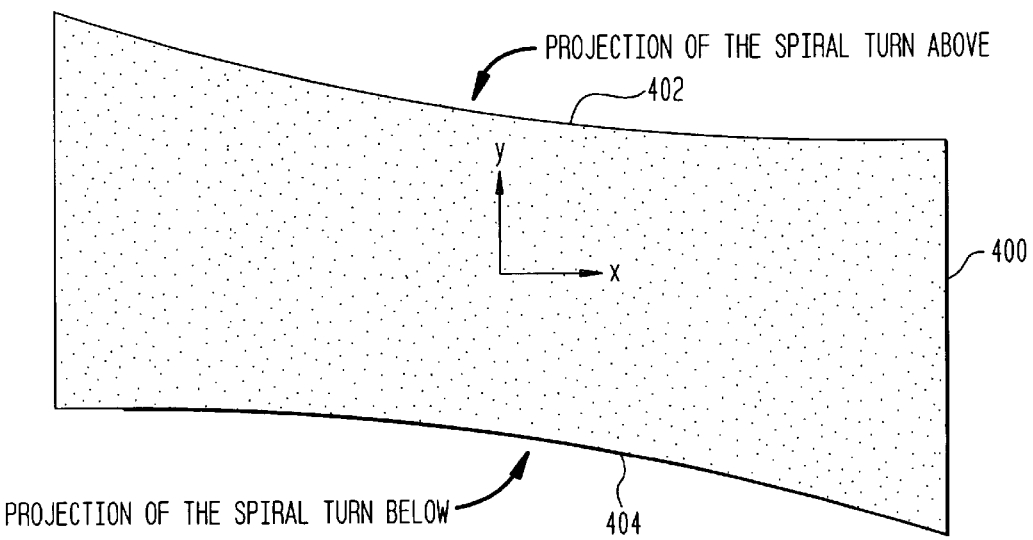
FIG. 4 illustrates a data-combination mask useful for processing cone beam data in accordance with the principles of the present invention.
Figure 3A:
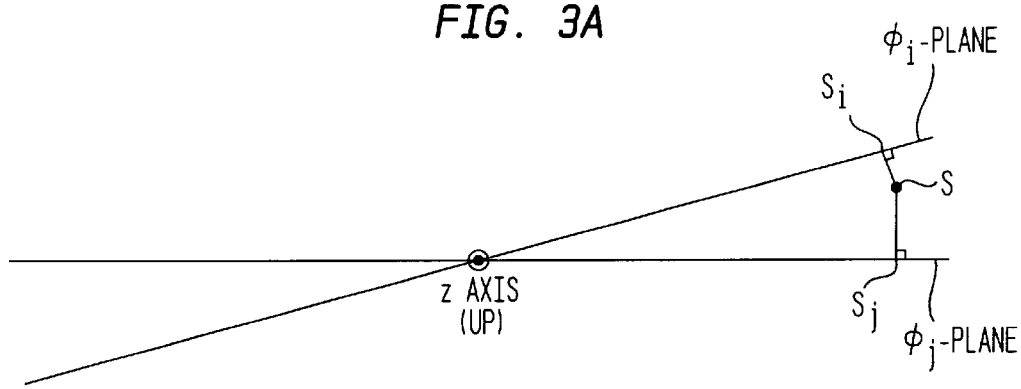
FIGS. 3A and 3B illustrate top and side views of the FIG. 2 projection for two different φ-planes.
Figure 3B:
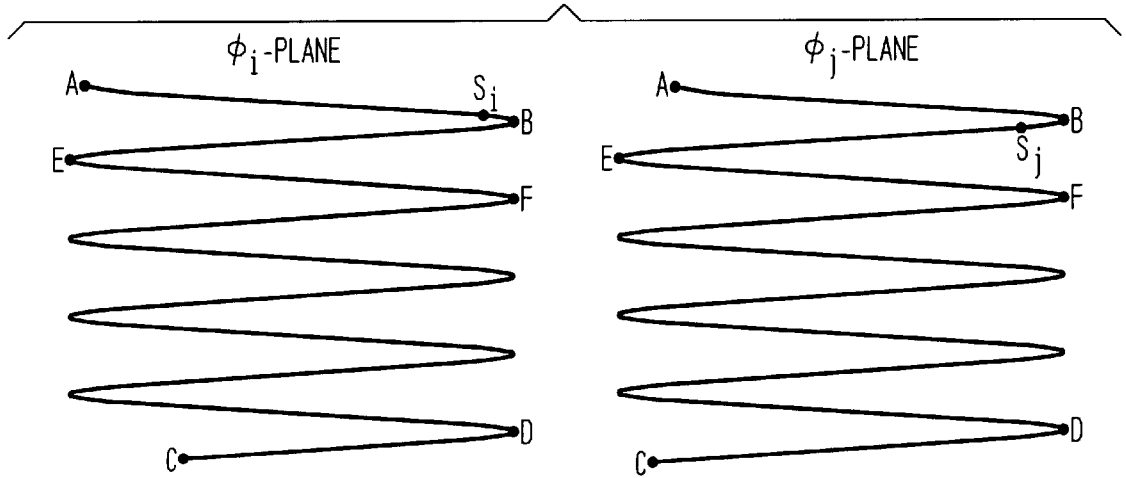

FIGS. 3A and 3B illustrate top and side views of the FIG. 2 projection for two different φ-planes, the $\phi_i$-plane and $\phi_j$-plane. Let S represent a position for the x-ray source which projects orthogonally to a point $S_i$ on the curve AB on the $\phi_i$-plane. On another φ-plane, for example where $\phi=\phi_j$ ($>\phi_i$), the projected spiral path has a different phase. As a result of the different phase, the source position S does not project onto a point $S_j$ on the uppermost stage of the projected spiral path, i.e., on curve AB, but instead, projects onto the spiral path just below curve AB, i.e., curve EB. Thus, some of the Radon data on the $\phi_i$-plane and some of the Radon data on the $\phi_j$-plane correspond to line segments intersecting the cone beam image captured by the detector when the source is at S. For that portion of the Radon data which is on the $\phi_j$-plane the length of the corresponding line segments should be limited by a data-combination mask. FIG. 4 illustrates a suitable data-combination mask 400, where the top curve 402 and the bottom curve 404 correspond to cone beam projections of the spiral turn above and below the source position S (shown as AB and EF, respectively, in FIG. 3B). Data-combination masks 400 are used for each set of the acquired cone beam data to ensure the coverage of the integration plane intersecting the ROI is properly partitioned between the various source positions which intersect that plane without overlap. Further details concerning the generation and use of data-combination masks can be found in the literature, such as the present inventor's forenoted U.S. Pat. No. 5,463,666 and his U.S. Pat. No. 5,504,792 entitled METHOD AND SSTEM FOR MASKING CONE BEAM PROJECTION DATA GENERATED FROM EITHER A REGION OF INTEREST HELICAL SCAN OR A HELICAL SCAN, both incorporated by reference herein. Line segments which have their length limited by the boarders of a data-combination mask will be hereinafter referred to as being "data-combination limited" line segments.

On the other hand, for the Radon data on the $\phi_i$-plane, the length of the corresponding line segments is determined, as noted above, by the requirement that the x-ray paths of the data do not traverse the overlaying objects that are outside of the local ROI on this $\phi$-plane. Consequently, referring specifically to FIG. 3B, where the z-axis is the vertical axis (i.e., in the plane of the paper), since $S_i$ is on curve AB, which is the uppermost edge of this local ROI, the "non-traversing" x-ray paths are those that strike the $\phi_i$-plane below curve AB, i.e., those that angle downward from an orthogonal projection of the source S (note, in FIG. 3B, S is located above the paper). We shall refer to lione segments having this kind of length limitation as being "ROI-edge limited". More precisely, for the Radon data on the $\phi_i$-plane, the upper end of this kind of line segment is ROI-edge limited, and the lower end is data-combination limited.

Thus, when calculating line integral derivative data in the cone beam image detected at S, some line segments calculated therein will be data-combination limited while others will be ROI-edge limited. In the Radon space driven approach described in the present inventor's U.S. Pat. No. 5,862,198 entitled A PRECALCULATED HITLIST FOR REDUCING RUN-TIME PROCESSING OF AN EXACT CONE BEAM RECONSTRUCTION ALGORITHM, these differences in line length are stored in a pre-calculated database which is used as a look up table, or "hitlist", for supplying the line length data for each line to be computed on each set of cone beam data, for developing contributions to Radon data samples. Although the use of the pre-calculated hitlist greatly speeds up the required signal processing, it still suffers from the forenoted drawbacks of Radon space driven approaches.

The present inventor has developed a technique which groups the line segments that are formed in the cone beam data in accordance with the manner in which their length is to be limited during the reconstruction processing. As will become apparent from the following description, since the inventive grouping is determined by a point $C_0$ on the data combination mask, the new technique is compatible not only with the detector driven approach to image reconstruction, but in fact it is facilitated.

Figure 5:
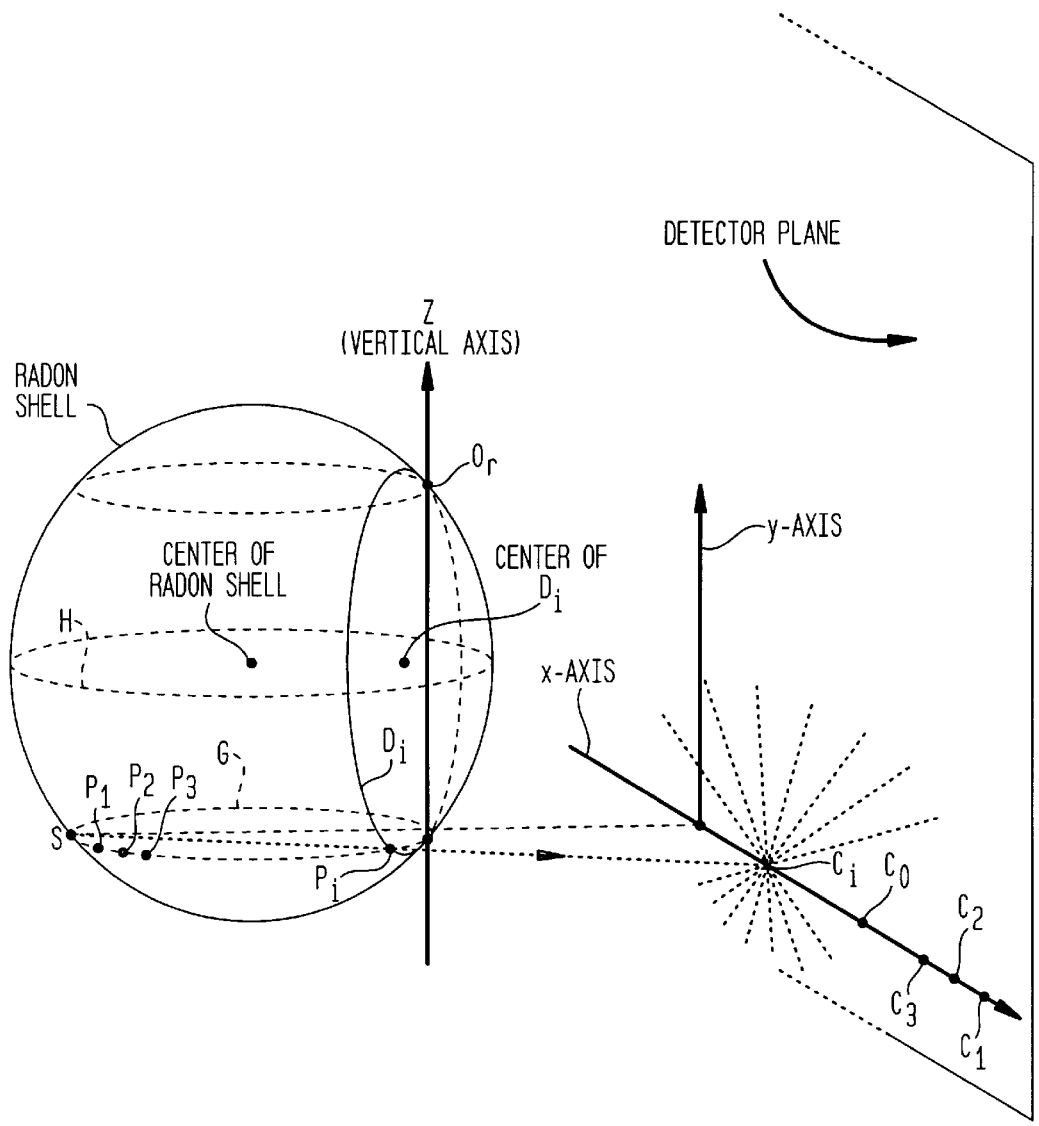
FIG. 5 illustrates geometry useful for understanding the basic principles of the invention.

Geometry useful for understanding the basic principle of the invention is shown in FIG. 5, which illustrates a Radon shell having a Radon space origin $O_r$, generated at a source position S. (The Radon shell is a spherical shell having a diameter $O_rS$, which is the locus in Radon space of all the Radon data that can be generated at the single source position S. For further understanding of the details of the Radon shell and its relation to Radon space driven image reconstruction processing, the reader is directed to the present inventor's prior U.S. Pat. No. 5,257,183). A horizontal plane which passes through the source position S will intersect the Radon shell in a circle G. It can be shown from geometry that each vertical plane $\phi_i$ coaxial with the z-axis, intersects the Radon shell in a circle $D_i$, where $D_i$ passes through the origin $O_r$, intersects the circle G at a point $P_i$, and has as its diameter a line segment $OP_i$. Let (x,y) be the coordinate system on the detector, with the (x,y) origin being $O_d$ located at the orthogonal projection of the source S onto the plane of the detector. Since the circle G contains the source S, the source projects circle G onto the detector plane as a line superimposed on the x-axis of the detector. Let $C_i$ denote the projection of the intersection point $P_i$ on the circle G onto the x-axis. As described in detail in the present inventor's above-noted U.S. Pat. No. 5,257,183, the Radon data on the circle $D_i$, and thus on the plane $\phi=\phi_i$, can be determined by calculating line integral derivative data for the lines on the detector which intersect the point $C_i$, such lines being shown in dashed form in FIG. 5. Accordingly, at this same source position, contribution to the Radon data of other $\phi$-planes can be calculated in a similar manner, as shown by $\phi$-plane intersection points $P_1$, $P_2$, and $P_3$, and processing of the cone beam data in lines that pass through corresponding points $C_1$, $C_2$, and $C_3$.

Thus, FIG. 5 illustrates two very important facts:
1) There is a one-to-one correspondence between the points on the x-axis and the $\phi$-planes on which the Radon data reside, i.e., each point $C_i$ determines some of the Radon data on a unique $\phi_i$-plane; and
2) The mapping from $\phi_i$ to $C_i$ is monotonic, i.e., for any point $C_i$ on the x-axis, all the points to the right correspond to lower values of $\phi_i$, and all the points to the left correspond to higher values. In the illustrated embodiment, $\phi_i$ is measured in an anti-clockwise direction about the z-axis.

These facts make it possible, as well as practical, to group line segments for which line integral derivative calculations are to be performed in each set of the cone beam data, according to the manner in which the line segments are to have their length limited. More specifically, in accordance with the principles of the present invention, a point $C_o$ is determined on the x-axis of the cone beam data acquired at each source position, which marks a location that defines two different groups of the line segments in accordance with how their length is to be limited.

Figure 6:
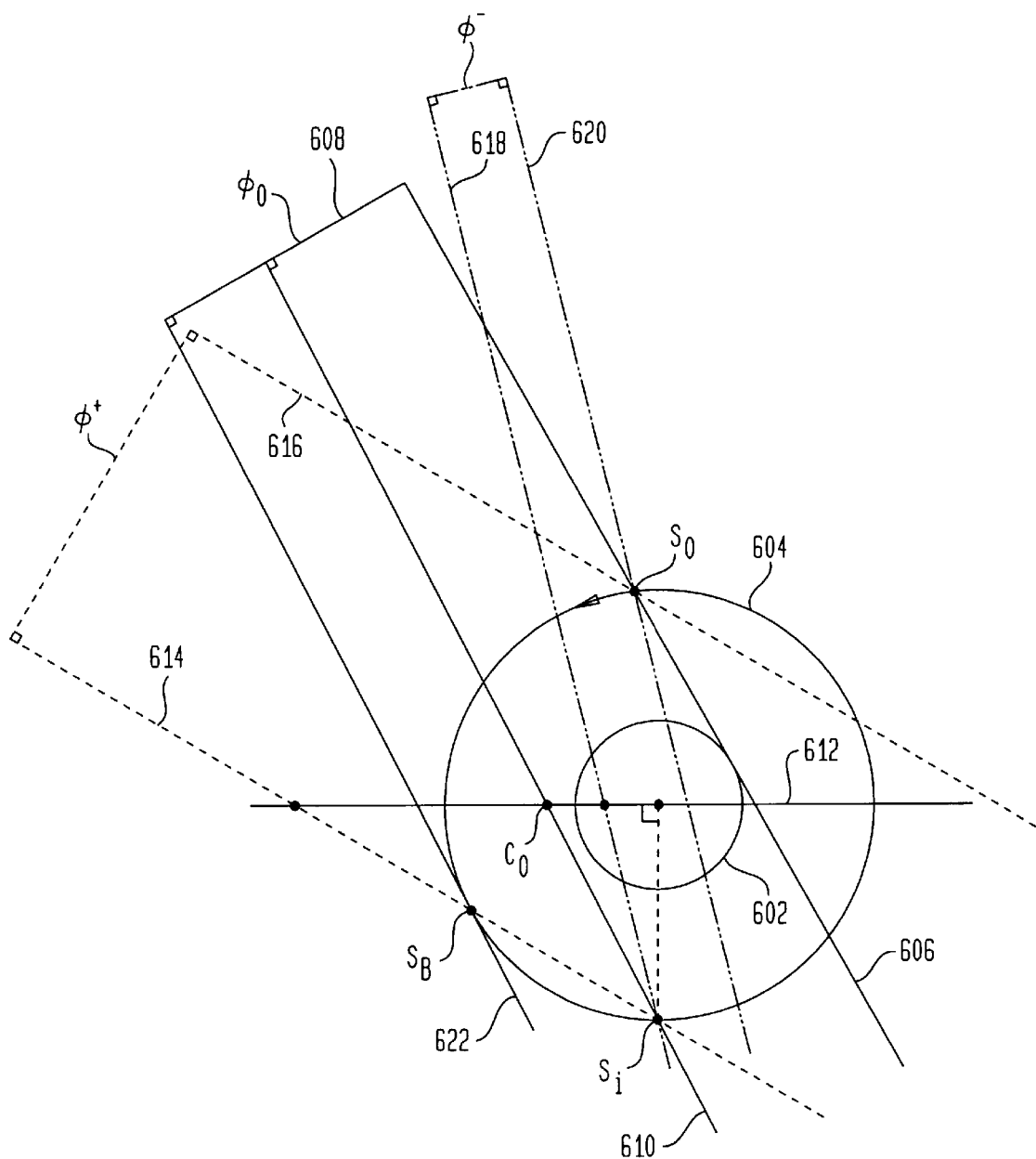
FIG. 6 illustrates a top view of a portion of the image reconstruction geometry shown in FIG. 5.

Accordingly, FIG. 6 illustrates a top view of a portion of the image reconstruction geometry, wherein a circle 602 is representative of the object and a circle 604 is representative of the spiral path traversed by the x-ray source S. A starting source position So is marked on scan path circle 604. In accordance with the previous description of FIG. 2, in order to provide an exact image reconstruction and avoid image artifacts, a parallel projection of the scan path must, at a minimum, begin and end outside of the local ROI of the object. Accordingly, a line 606 is drawn starting from source position So so as to be tangential to circle 602 (i.e., touching the outside edge of object 16). The Radon space $\phi$-plane which forms an orthogonal intersection with line 606 defines the Radon space $\phi_0$-plane, which is labeled 608.

The following analysis describes how to determine the point $C_o$ in the data acquired at any source position $S_i$, starting from and including the starting source position $S_0$. First, assume an anti-clockwise rotation of the source S, and mark source position $S_i$ on scan path circle 604. Next, one draws a line 610 which passes through source position $S_i$ and is parallel with line 606, and therefore also bears an orthogonal relationship to the Radon space $\phi_0$-plane 608. Then, $C_0$ is defined as that point on the x-axis in the detector plane that acquires the cone beam data at source position $S_i$ (i.e., detector plane 612, which bears an orthogonal relationship to a line, shown dashed, from source position $S_i$ to the center of object circle 602), which is intersected by line 610. This $C_0$ corresponds to the $C_0$ previously described and shown in FIG. 5 and which is used, in accordance with the principles of the present invention to group the line segments formed in the cone beam data during image reconstruction processing, in accordance with the manner of their length limitation. In this manner, the location of $C_0$ for all of the source positions S can be determined. (The anti-clockwise rotation assumed in the above analysis can be easily modified for the opposite sense of source rotation.)

Figure 7A:
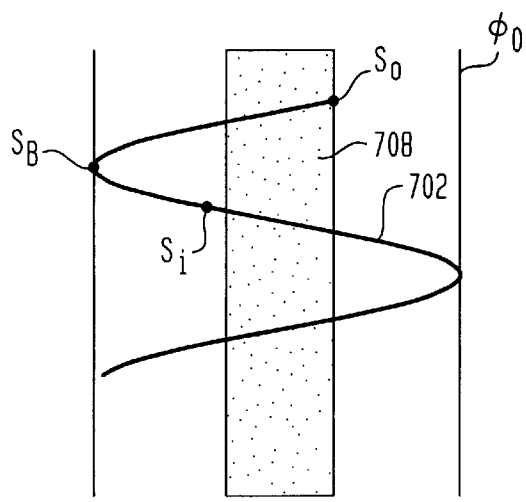
FIGS. 7A, 7B, and 7C each illustrate a parallel projection of the spiral scan path onto a representation of the ROI for a respective one of the three Radon space φ-planes illustrated in FIG. 6.
Figure 7B:
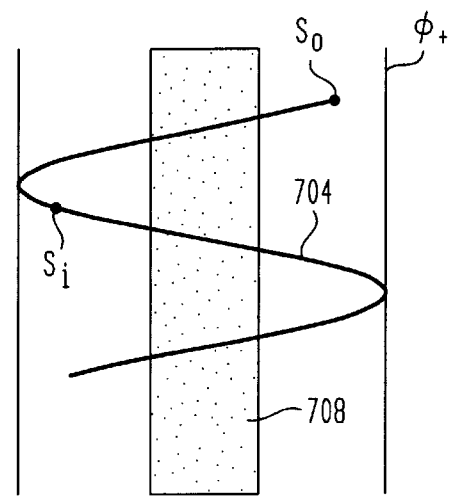
Figure 7C:
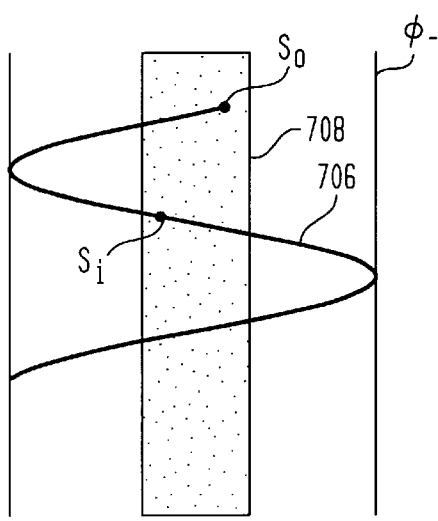

Before describing in detail various ways to use the point $C_0$ to aid image reconstruction processing in accordance with the invention, for additional understanding of the present invention the reader is referred to FIGS. 7A, 7B, and 7C. These Figures illustrate a parallel projection of the spiral path onto a representation of the ROI for source positions $S_0$ and $S_i$, for the three Radon space $\phi$-planes illustrated in FIG. 6, namely the $\phi_o$-plane 608 and the $\phi$-planes that are just ahead ($\phi^+$) and just behind ($\phi_-$) the $\phi_o$-plane, respectively. The parallel projection of the spiral path onto each of the $\phi$-planes manifests itself in FIGS. 7A, 7B, and 7C in the form of sinusoidal curves 702, 704, 706, respectively, whose phase depends on the angular orientation of the particular $\phi$-plane. As was shown in FIG. 6, since line 606 is tangential to object circle 604, the starting source position $S_0$ in FIG. 7A resides at the beginning of the uppermost turn of curve 702, which just touches the outside edge of the ROI 708 in the object. As also shown in FIG. 6, a line 622 tangent to scan path 604 and which intersects the $\phi_o$-plane, marks the location of a source position $S_B$, in FIG. 7A. Since source position $S_i$ occurs on the scan path after source position $S_B$, it necessarily resides on the next lower turn of curve 702. Note, consistent with the position of solid line 610 passing outside of object circle 602, source position $S_i$ also resides outside of ROI 708. Accordingly, when calculating line integral data for the $\phi_o$-plane (for Radon space driven reconstruction processing), or when calculating line integral data representative of the Radon space $\phi_o$-plane (for detector driven reconstruction processing), because source position $S_0$ resides on an uppermost turn of the spiral scan path, calculation of the line integral data in the cone beam data acquired at source position $S_0$ requires use of ROI-edge limited line segments L, whereas the line segments L calculated in the cone beam data acquired at source position $S_i$ will be data combination limited.

In FIG. 7B (illustrating a $\phi^-$-plane), as evident from the dashed lines 614 and 616 of FIG. 6 which pass through the source positions $S_0$ and $S_i$ and are orthogonal to the $\phi^-$-plane, source position $S_0$ resides on the uppermost turn of curve 704 and is well outside the outer edge of ROI 708, and source position $S_i$ resides on the next lower turn of curve 704. Accordingly, calculation of the line integral data in the cone beam data acquired at source position $S_0$ requires use of ROI-edge limited line segments L, and the line segments L calculated in the cone beam data acquired at source position $S_i$ will be data combination limited.

In FIG. 7C (illustrating a $\phi^-$-plane), as evident from the dashed lines 618 and 620 of FIG. 6 which pass through the source positions $S_0$ and $S_i$ and are orthogonal to the $\phi^-$-plane, source position $S_0$ resides on the uppermost turn of curve 706, however it now resides well inside the outer edge of ROI 708, and source position $S_i$ resides on the next lower turn of curve 704. As was described in conjunction with FIG. 2, the range of the scan path projections at the upper and lower ends or the ROI must begin and end, respectively, outside of the local ROI. In this case, it is clear that source position $S_0$ begins inside the ROI, and therefor none of the data from source position $S_0$ can be used for calculating line integral data for the $\phi^-$-plane. However, since source position $S_i$ resides on the next lower turn of curve 706, and this segment of curve 706 now corresponds to the uppermost curve, its data can be used to calculate line integral data. Thus, for the $\phi^-$-plane, the line segments L calculated in the cone beam data acquired at source position $S_i$ will be ROI-edge limited line segments.

As is apparent from FIG. 7C, when calculating line integral derivative data in the cone beam data, at some source positions some of the line segments will have no length, while other line segments will be ROI-edge limited. This effect can be easily shown by referring to FIG. 8, which illustrates the first and last $2\pi$ (360°) of the source scan path geometry. As is apparent from the above description, only the source positions in the first or the last $3\pi/2+\alpha/2$ of the spiral scan path, where $\alpha$ is the fan angle of the x-ray beam, ever appear in the uppermost or the lowermost turns of the sinusoidal curve defining a local ROI. More specifically, in section "a", corresponding to the first $\pi/2+\alpha/2$ degrees of rotation, Radon derivative data determined using line segments L to the left of $C_0$ (where $C_0$ is calculated in accordance with the present invention) will not be calculated (because the line segments L will have zero length), while Radon derivative data determined using line segments L to the right of the $C_0$ will be calculated using ROI edge-limited line segments. In section "b", corresponding to the next $\pi$ degrees of rotation, Radon derivative data determined using line segments L to the right of the calculated $C_0$ will be determined using line segments L that are ROI edge-limited, while Radon derivative data determined using line segments L to the left of the $C_0$ will be calculated using data-combination limited line segments. In section "c", corresponding to the last $\pi/2-\alpha/2$ degrees of rotation, Radon derivative data determined using line segments L, both to the left and right to of the calculated $C_0$, will be calculated using line segments L that are data-combination limited. Accordingly, only the cone beam data captured at source positions in the FIG. 8 ranges a and b in the turns near the upper and lower bounds of the ROI need be processed with the inventive procedure described above, to limit the line integrals for Radon derivative computation. The cone beam data captured at all the intermediate source positions can be processed with a conventional data-combination procedure, such as described in U.S. Pat. Nos. 5,504,792 and 5,748,697.

FIGS. 9, 10 and 11, 12 illustrate grouping of lines formed in the acquired sets of cone beam data, in accordance with the principles of the invention, as described above, for image reconstruction processing in a Radon space driven and a detector driven approach, respectively.

Figure 8:
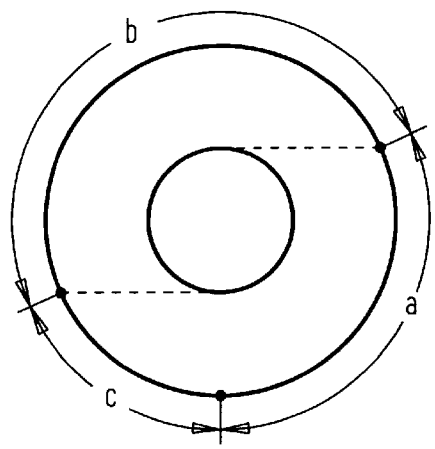
FIG. 8 illustrates a portion of the image reconstruction geometry shown in FIG. 6, useful for understanding FIG. 7.
Figure 9:
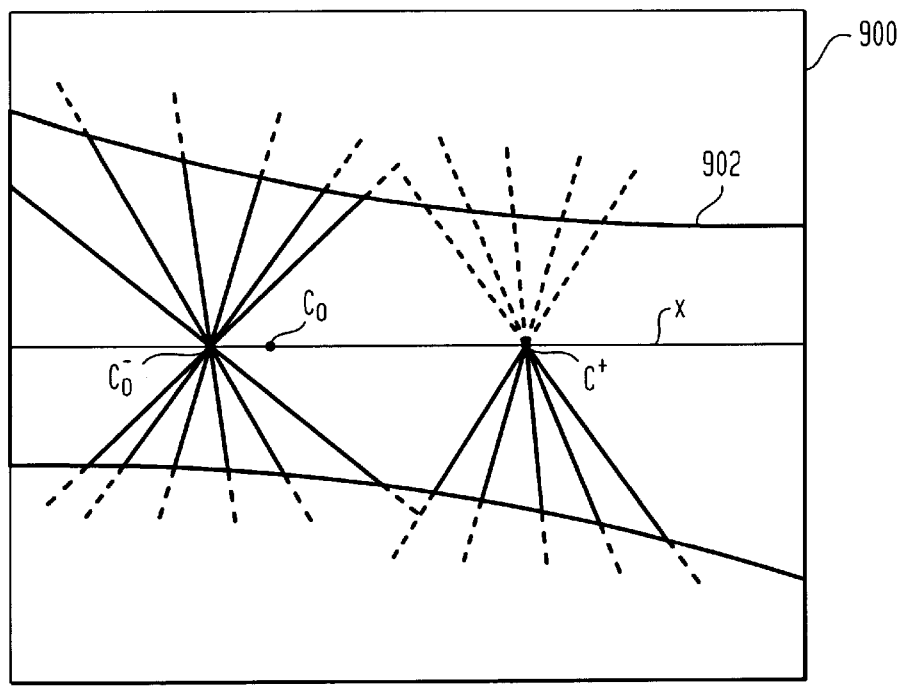
FIGS. 9 and 10 illustrate grouping of lines formed in the acquired sets of cone beam data, in accordance with the principles of the invention, for use in Radon space driven approaches to image reconstruction.

Referring first to FIG. 9, a set of cone beam data 900 is shown which is acquired at a given source position $S_i$ acquired during the first turn of the spiral path, but after the first $\pi/2+\alpha/2$ degrees of rotation (i.e., a point in section "b" of FIG. 8). The point $C_0$ is marked on the x-axis of the data using the procedure described above in conjunction with FIG. 6. Next, an appropriate data combination mask 902 is applied to the data, and then line integral derivative calculations are ready to be performed on specific line segments formed in the acquired cone beam data. The general technique for performing the line integral derivative calculations is described in FIGS. 4 and 5 herein, and in greater detail in the present inventor's earlier U.S. Pat. No. 5,748,697. However, in accordance with the present invention, once the point $C_0$ is marked on the x-axis of the data, all of the line segments that intersect the x-axis to one side of point $C_0$ will have both of their ends determined by the upper and lower boundaries of mask 802 (i.e., data-combination limition), and all of the line segments that intersect the x-axis to the other side of point $C_0$ will have one of their ends determined by one of the upper or lower boundaries of the mask (depending upon whether the current source position is near the lower or upper edge, respectively, of the ROI), and its other end determined by the x-axis of the mask (i.e., ROI-edge limitation). Thus, with apparatus in accordance with the invention, circle scans are not required at the top and bottom edges of the ROI. The remainder of the image reconstruction processing can be conventional, as described in detail, for example, in the forenoted U.S. Pat. No. 5,748,697, or can use a pre-calculated "hitlist" for further reducing the complexity of the Radon space driven data processing, as described in the present inventor's U.S. patent application Ser. No. 08/940,489 entitled A REDUCTION OF HITLIST SIZE IN SPIRAL CONE BEAM CT BY USE OF LOCAL RADON ORIGINS.

Figure 10:
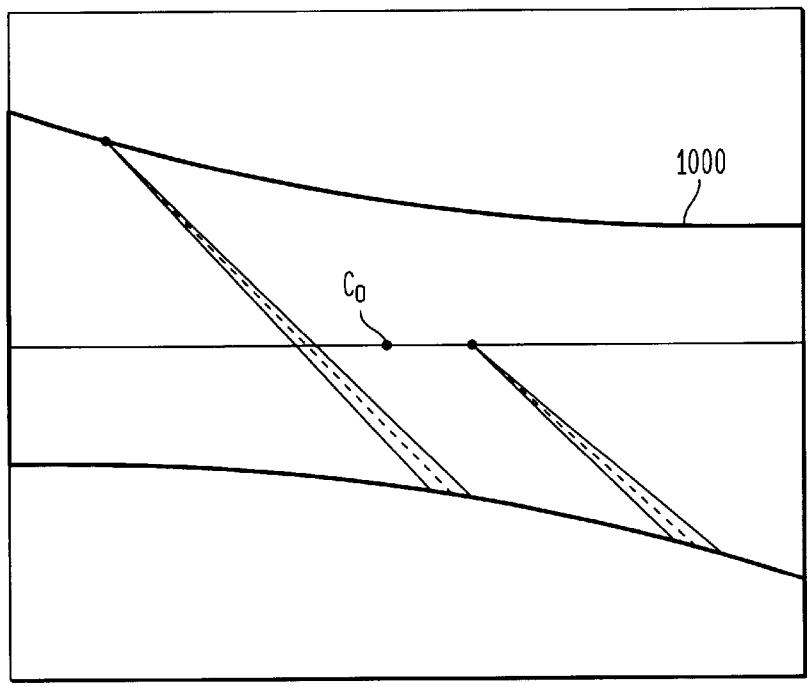

FIG. 10 illustrates use of the present invention when the line integral derivative calculations are performed using a rotation operation for the line segments L. In a manner similar to that described for FIG. 9, all of the line segments that intersect the x-axis to one side of point $C_0$ will have both of their ends determined by the upper and lower boundaries of mask 1000, and all of the line segments that intersect the x-axis to the other side of point $C_0$ will have one of their ends determined by one of the upper or lower boundaries of the mask (depending upon whether the current source position is near the lower or upper edge, respectively, of the ROI), and its other end determined by the x-axis of the mask.

Figure 11A:
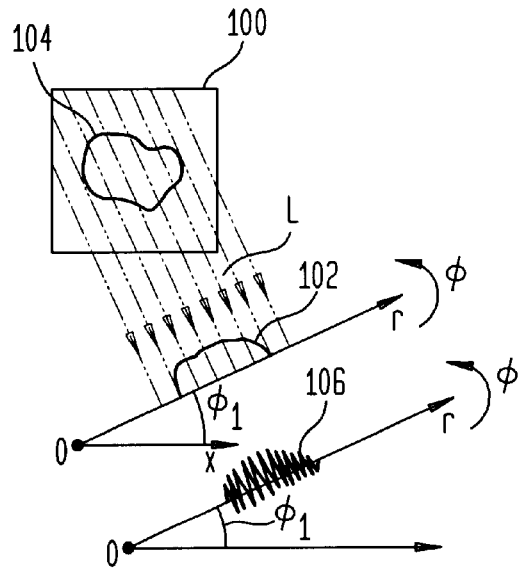
FIGS. 11A and 11B illustrate a 3D backprojection approach for image reconstruction.
Figure 11B:
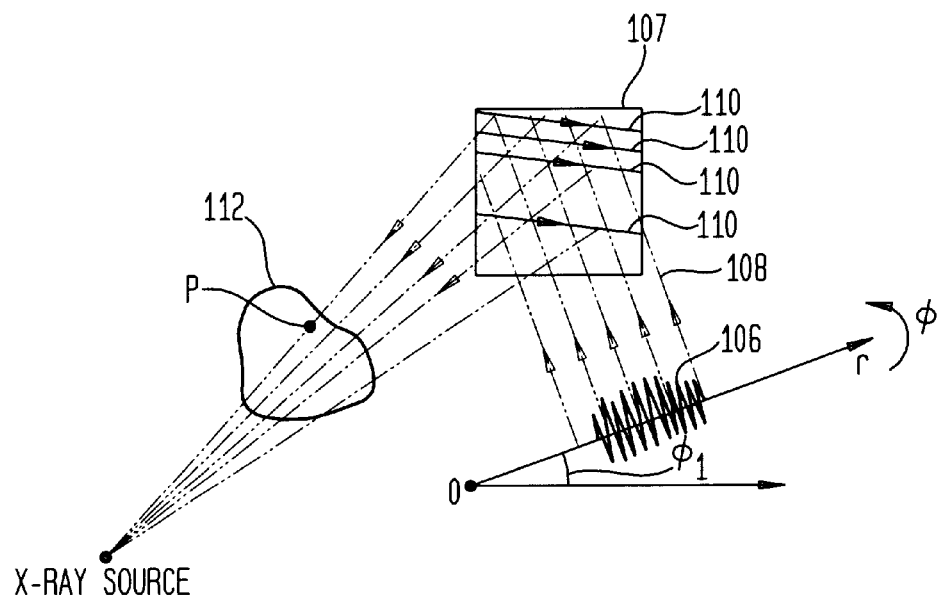
Figure 12:
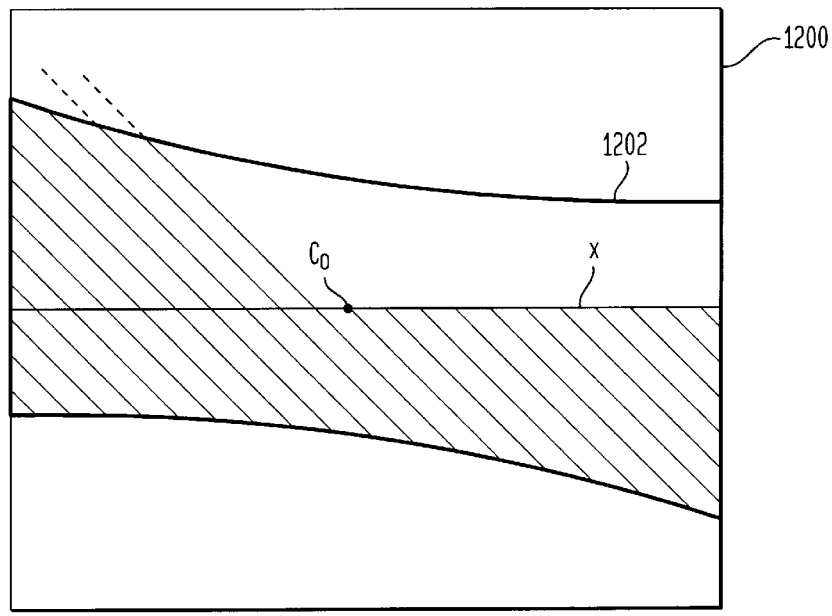
FIG. 12 illustrates grouping of lines formed in the acquired sets of cone beam data, in accordance with the principles of the invention, for use in the 3D backprojection approach to image reconstruction illustrated in FIGS. 11A and 11B.

Application of the invention to the detector driven image reconstruction approach, shown in FIGS. 11 and 12, represents an especially preferred embodiment of the invention. More specifically, in this approach, a filtered backprojection (FBP) cone beam image reconstruction technique is used, such as described by Kudo, H. and Saito, T. in their article entitled "Derivation and Implementation of a Cone-Beam Reconstruction Algorithm for Nonplanar Orbits", IEEE Trans. Med. Imag., MI-13 (1994) 196–211, and as described in the present inventor's forenoted U.S. patent application Ser. No. 09/052,281, both incorporated by reference herein.

Briefly, the FBP reconstruction technique, illustrated by FIGS. 11A and 11B, consists of the following steps for processing the cone beam data acquired at each of the source positions $S_i$:

1. Compute a 1D projection (i.e., a line integral) of the cone beam image acquired on a detector plane 100, at each of a plurality of angles $\theta$. This step is illustrated in FIG. 11A for a given angle $\theta_1$ of a plurality of angles $\theta$. A 1D projection 102 is shown at coordinates r, $\theta_1$ comprising the integrated values of the cone beam image 104 on detector plane 100 along a plurality of parallel lines $L(r,\theta)$ that are normal to angle $\theta_1$, each line L being at an incremental distance r from an origin O. Generally, if the detector plane 100 comprises an N by N array of pixels, then the number of angles $\theta$ is typically given by $\pi N/2$.

2. Filter each 1D projection 102 in accordance with a d/dr filter, resulting in a new set of values at each of the r,$\theta$ coordinates, such as shown by the derivative projection 106 for the angle $\theta_1$ shown in FIG. 11A. Note, the resulting values at these r,$\theta$ coordinates yield a quantity proportional to the Radon derivative for the integration plane $Q(r,\theta)$, as described above for Radon space driven image reconstruction processing.

Figure 13:
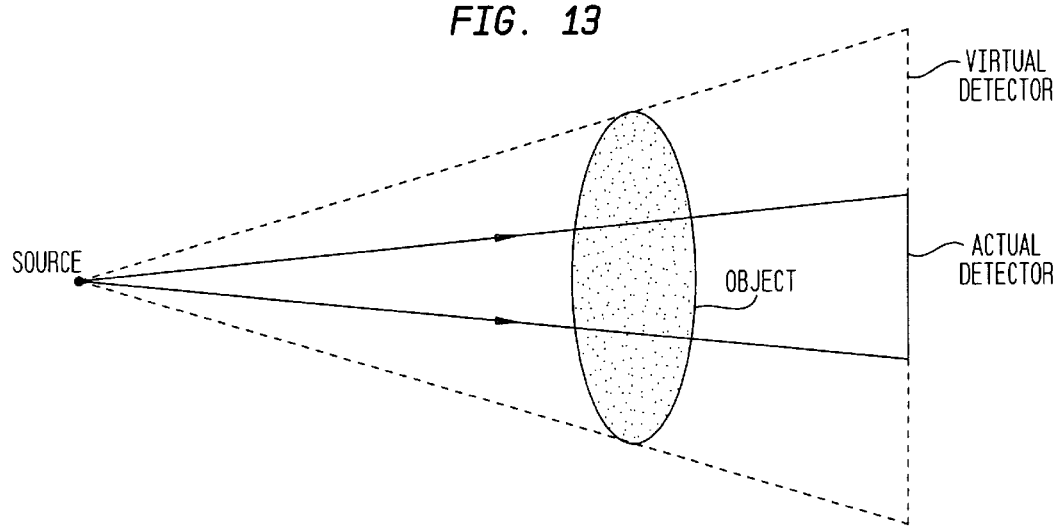
FIG. 13 illustrates a virtual detector for the 3D backprojection approach shown in FIGS. 11A and 11B.

3. As illustrated by FIG. 11B, the next step comprises backprojection of the derivative projection 106 from each angle 0 into a 2D object space 107 (which coincides with the detector plane 100). Lines 108 are representative of this backprojection, and spread the value from each r coordinate into the 2D space 107 in a direction normal to each $\theta$. Note, 2D object space 107 has a size corresponding to a virtual detector which is enlarged (compared with detector 12 of FIG. 1), so as to cover the entire ROI in the object. This enlargement of 2D object space 107 is illustrated in FIG. 13. This enlargement is required because the calculated Radon data affects the reconstruction of the entire Q plane, and not just the partial plane represented by the data combination mask.

4. Perform a 1D d/dt filtering of the backprojection image formed in 2D space 107 by step 3. The 1D filtering is performed in the direction of the scan path, i.e., along lines 110, where t points in the direction of the projection of the scan path.

5. Perform a weighted 3D backprojection of the resulting data from 2D space 107 (i.e., from each pixel in the detector) onto a plurality of sample points P in a 3D object volume 112. The density assigned to each point P is weighted by the inverse of the square of the distance between the sample point and the location of the x-ray source (see Equation 59 of the forenoted Kudo et al article).

Thus, for application of the FBP image reconstruction technique to the present invention, as shown in FIG. 12, in a set of cone beam data 1200 acquired at a given source position $S_i$, the point $C_0$ is marked on the x-axis. The technique for marking the point $C_0$ is the same as noted above for FIG. 9. Next, an appropriate data combination mask 1202 is applied to the cone beam data, and a plurality of lines L are formed in each set 1200 of the acquired cone beam data in accordance with Step 1 of FIG. 11A. In accordance with the principles of the present invention, the endpoints (and hence the length) of the line segments L are determined in the same manner as described above in FIG. 9, resulting in all of those line segments crossing the x-axis to the right of $C_0$ to be ROI-edge limited, and all of those line segments crossing the x-axis to the left of $C_0$ to be data-combination limited. Thereafter, the line segments L are processed, as briefly described above in FIGS. 11A and 11B, and as described in greater detail in the present inventor's forenoted U.S. patent application Ser. No. 09/052, 281, for making a 3D image reconstruction of the ROI in the object. Again, note that even in a detector driven image reconstruction approach, with apparatus in accordance with the present invention, circle scans are not required at the top and bottom edges of the ROI.

Thus, there has been shown and described a novel 3D CT imaging method and apparatus for obtaining an exact image reconstruction without the requirement of top and bottom circle scans, by grouping line segments L formed in the acquired cone beam data according to how their length is to be limited. Many changes, modifications, variations and other uses and applications of the subject invention will, however, become apparent to those skilled in the art after considering this specification and its accompanying drawings, which disclose preferred embodiments thereof For example, as previously noted, the invention finds use in both the Radon space driven and detector driven image reconstruction processing. Furthermore, the scan path could have non-uniform pitch and other variations. All such changes, modifications, variations and other uses and applications which do not depart from the teachings herein are deemed to be covered by this patent, which is limited only by the claims which follow as interpreted in light of the foregoing description.

What is claimed is:

1. A method for performing three dimensional computerized tomographic imaging of a region-of-interest (ROI) in an object using a cone beam source of radiation energy, comprising the steps of:

defining a source scanning trajectory as a scan path that encircles the ROI in the object and is traversed by the cone beam source;

using the cone beam source, fixed relative to an area detector with both source and detector movably positioned relative to the object, for applying radiation energy towards the object from a plurality of source positions along the scan path as said source traverses the scan path, said applying causing said area detector to acquire cone beam projection data corresponding to respective portions of the object at each of said source positions;

masking the cone beam projection data acquired at each of said source positions with a mask having upper and lower boundaries formed by cone beam projections onto the plane of the detector of portions of the source scan path that are above and below, respectively, the source position that acquired the data being masked;

calculating data for each of a plurality of line segments L formed in the masked cone beam projection data acquired at each of said source positions, said mask being used during said calculating step to divide said plurality of line segments L into separate groups, each group having a different technique for limiting the length of the line segments L therein; and reconstruction processing the data calculated for said line segments L having their length determined by the mask as defined above, for reconstructing a 3D image of the ROI in the object.

2. The method of claim 1, wherein the calculating step uses said mask when processing line segments L formed in the cone beam data acquired near the top or bottom edges of the local ROI, to divide said line segments L into:

a first group that has both endpoints of the line segments L determined by the upper and lower boundaries of the mask, and a second group that has one of the endpoints of the line segments L determined by one of the upper or lower boundaries of the mask, and its other end point determined by an axis of the mask.

3. The method of claim 1, wherein the calculating step calculates line integral data for each of said line segments L.

4. The method of claim 3, wherein the calculating step calculates a derivative of the line integral data for each of said line segments L.

5. The method of claim 4, wherein the calculating step calculates line integral derivatives for a plurality of said line segments L which are spaced along each of a plurality of lines $(r,\theta)$, each line having a different angular position $(\theta)$ with respect to a coordinate system defined on the detector.

6. The method of claim 1, wherein the calculating step includes a step for determining a point $(C_0)$ on an axial line crossing the mask which intersects a projection of the source position that acquired the data.

7. The method of claim 6, wherein during said calculating step, those of said line segments L formed in the masked cone beam data which cross said axial line to one side of $C_0$ have their length limited using one technique, and those of said line segments L which cross said axial line to the other side of $C_0$ have their length limited using another technique.

8. The method of claim 7, wherein said one technique comprises determining both endpoints of the line segments L using the upper and lower boundaries of the mask, and said other technique determines one of the endpoints of the line segments L using one of the upper or lower boundaries of the mask, and its other end point is determined using the axial line of the mask.

9. The method of claim 1, wherein:

said calculating step calculates line integral derivative data for each of said line segments L, and said reconstruction processing step comprises accumulating the derivative data in Radon space, and inversion processing of the accumulated Radon data for reconstructing an image of the ROI in the object.

10. The method of claim 1, wherein:

said calculating step calculates line integral derivative data for each of said line segments L, and said reconstruction processing step comprises 2D backprojecting the line integral derivatives calculated for a plurality of said line segments L onto a 2D space corresponding to the plane of the detector, and 3D backprojecting the 2D backprojection results into a 3D space, thereby reconstructing a 3D image of the ROI in the object.

11. The method of claim 5, wherein the calculating step calculates said line integral derivatives by forming a line segment adjacent each side of each line segment L using a small angle rotation about one endpoint of each of said line segments L, calculating a line integral for each such adjacent line segment, and subtracting said calculated line integrals from each other.

12. The method of claim 5, wherein the calculating step calculates said line integral derivatives by forming a parallel line segment to each side of each line segment L using a small perpendicular shift from about each of said line segments L, calculating a line integral for each such parallel line segment, and subtracting said calculated line integrals from each other.

13. The method of claim 1, wherein the source scanning trajectory is defined as a spiral scan path that surrounds the ROI in the object.

14. The method of claim 10, wherein after completion of the 2D backprojecting step, a 1D d/dt filtering step is performed on the results in said 2D space along lines in the direction of a projection of the scan path.

15. The method of claim 13, wherein the 3D backprojecting step comprises performing a weighted 3D backprojection of the 1D d/dt filtering results at discrete points along said lines onto a plurality of sample points in a 3D object volume.

16. The method of claim 15, wherein the weight assigned to each sample point in the 3D object volume is the inverse of the square of the distance between each sample point and the location for the cone beam source in the 3D volume.

17. The method of claim 10, wherein the 2D backprojecting step comprises 2D backprojecting the calculated line integral derivatives onto a virtual 2D space in the plane of the detector having a height that is greater than the height of said area detector.

18. The method of claim 17, wherein the height of said virtual 2D space is sufficient to cover the entire field-of-view of the ROI in the object.

19. Apparatus for performing three dimensional computerized tomographic imaging of a region-of-interest (ROI) in an object using a cone beam source of radiation energy, comprising:

a source of cone beam radiation energy;

a manipulator for providing a source scanning trajectory as a scan path that encircles the ROI in the object and causes the source and detector to traverse the scan path;

means for causing the source to apply radiation energy towards the object from a plurality of source positions along the scan path as said source traverses the scan path, said area detector acquiring cone beam projection data corresponding to respective portions of the object at each of said source positions; and an image reconstruction processor for, applying a mask to the cone beam projection data acquired at each of said source positions, said mask having upper and lower boundaries formed by cone beam projections onto the plane of the detector of portions of the source scan path that are above and below, respectively, the source position that acquired the data being masked;

calculating data for each of a plurality of line segments L formed in the masked cone beam projection data acquired at each of said source positions, said mask being used during said calculating step to divide said plurality of line segments L into separate groups, each group having a different technique for limiting the length of the line segments L therein; and reconstruction processing the data calculated for said line segments L having their length determined by the mask as defined above, for reconstructing a 3D image of the ROI in the object.

* * * * *